(12) United States Patent
Riester et al.

(10) Patent No.: US 10,596,192 B2
(45) Date of Patent: Mar. 24, 2020

(54) TREATING ROTATOR CUFF CONDITIONS

(71) Applicant: Mayo Foundation for Medical Education and Research, Rochester, MN (US)

(72) Inventors: Scott M. Riester, Rochester, MN (US); John W. Sperling, Rochester, MN (US); Andre J. van Wijnen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/745,354

(22) PCT Filed: Jul. 15, 2016

(86) PCT No.: PCT/US2016/042531
§ 371 (c)(1),
(2) Date: Jan. 16, 2018

(87) PCT Pub. No.: WO2017/011762
PCT Pub. Date: Jan. 19, 2017

(65) Prior Publication Data
US 2018/0200294 A1 Jul. 19, 2018

Related U.S. Application Data

(60) Provisional application No. 62/193,476, filed on Jul. 16, 2015.

(51) Int. Cl.
| | | |
|---|---|---|
| *A61K 33/30* | (2006.01) | |
| *A61P 19/04* | (2006.01) | |
| *A61K 9/00* | (2006.01) | |

(52) U.S. Cl.
CPC ............ *A61K 33/30* (2013.01); *A61K 9/0019* (2013.01); *A61P 19/04* (2018.01)

(58) Field of Classification Search
None
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 5,939,388 A | 8/1999 | Rosen et al. | |
| 6,187,742 B1 | 2/2001 | Wozney et al. | |
| 2003/0134308 A1 | 7/2003 | Clark et al. | |
| 2008/0027470 A1 | 1/2008 | Hart et al. | |
| 2010/0150885 A1 | 6/2010 | Tseng et al. | |
| 2011/0066242 A1 | 3/2011 | Lu et al. | |
| 2012/0328700 A1* | 12/2012 | Hill .................... | A61K 38/1875 424/488 |
| 2013/0303620 A1 | 11/2013 | Burch et al. | |
| 2017/0128534 A1 | 5/2017 | Riester et al. | |

FOREIGN PATENT DOCUMENTS

| | | |
|---|---|---|
| JP | 2009-542681 | 12/2009 |
| JP | 2012-126720 | 7/2012 |
| WO | WO 1991/011465 | 8/1991 |
| WO | WO 2010/131038 | 11/2010 |

OTHER PUBLICATIONS

Shin, The Korean Journal of Pain, 24, 2, 2011 (Year: 2011).*
Ahn et al., "Differences of RNA expression in the tendon according to anatomic outcomes in rotator cuff repair," *Am J Sports Medicine.*, 45(13):2995-3003, Nov. 2017.
B.J.F. et al., "A systematic review of the histological and molecular changes in rotator cuff disease," *Bone Joint Research.*, 1(7):158-166, Jul. 23, 2012.
Barbas et al.., "Combinatorial immunoglobulin libraries on the surface of phage (Phabs): Rapid selection of antigen-specific fabs," *Methods.*, 2(2):119, Apr. 1991.
Barnes et al., "Purification of Immunoglobulin G (IgG)", *Methods.*, 10:79-104, 1992.
Caring Medical Regenerative Medicine Clinics, "Prolotherapy for shoulder pain" (Oct. 18, 2011) [online] [retrieved on Sep. 15, 2016]. Retrieved from the Internet <URL: https://www.youtube.com/watch?v=eXI3cJQQKUA.
Caring Medical Regenerative Medicine Clinics, "Prolotherapy" (Apr. 12, 2015) [online] [retrieved on Sep. 15, 2016]. Retrieved from the Internet URL: http://vi'eb.archive.org/web/20150412171914/http://viww.caringmedical.com/prolofherapy/.
Carter et al., "Humanization of an anti-p185HER2 antibody for human cancer therapy," *Proc. Natl. Acad. Sci.USA.*, 89(10):4285-4289, May 15, 1992
Chaudhury et al., "Gene expression profiles of changes underlying different-sied human rotator cuff tendon tears," *J Shoulder Elbow Surgery.*, 25(10):1561-1570, Apr. 27, 2016.
Chaudhury et al., "Lessons we can learn from gene expression patterns in rotator cuff tears and tendinopathies," *J Shoulder Elbow Surgery.*, 21(2):191-199, 2012.
Dall'Acqua et al., "Antibody humanization by framework shuffling," *Methods.*, 36:43-60, May 2005.
Damschroder et al., "Framework shuffling of antibodies to reduce immunogenicity and manipulate functional and biophysical properties," *Mol Immunol.*, 44:3049-3060, 2007.
Deborah Gordon, "Rotator Cuff Injury and Regenerative Injection Therapy" Jan. 6, 2013, retrieved online on Jul. 20, 2017, Retrieved from the Internet, URL: http://www.drdeborahmd.com/rotator-cuff-injury-and-regenerative-injection-therapy.
Green et al., "Antigen-specific human monoclonal antibodies from mice engineered with human Ig heavy and light chain YACs," *Nature Genet.*, 7:13-21, 1994.
Green et al., "Production of Polyclonal Antisera", *Immunochemical Protocols*, Humana Press, pp. 1-5, 1992.
Griffiths et al., "Isolation of high affinity human antibodies directly from large synthetic repertoires," *EMBO J.*, 13(14):3245-3260, Jul. 15, 1994.
Gulotta et al., "Bone marrow-derived mesenchymal stem cells transduced with scleraxis improve rotator cuff healing in a rat model," *Am J Sports Med.*, 39(6):1282-1289, Jun. 2011.

(Continued)

*Primary Examiner* — Susan T Tran
*Assistant Examiner* — William Craigo
(74) *Attorney, Agent, or Firm* — Fish & Richardson P.C.

(57) ABSTRACT

This document provides methods and materials related to treating rotator cuff conditions (e.g., rotator cuff tendonitis or rotator cuff injuries such as partial rotator cuff tears). For example, methods and materials for using zinc or a zinc chelator to treat rotator cuff conditions are provided.

10 Claims, No Drawings

(56) References Cited

OTHER PUBLICATIONS

He et al., "Thiomyristoyl peptides as cell-permeable Sirt6 inhibitors," *Org Biomol Chem.*, 12(38):7498-7502, Oct. 14, 2014.
Huse et al., "Generation of a large combinatorial library of the immunoglobulin repertoire in phage lambda," *Science.*, 246(4935):1275-1281, Dec. 8, 1989.
Hwang et al., "Use of human germline genes in a CDR homology-based approach to antibody humanization," *Methods.*, 36:35-42, May 2005.
International Preliminary Report on Patentability of the International Application No. PCT/US2016/42531, dated Jan. 16, 2018, 6 pages.
International Search Report and Written Opinion of the International Application No. PCT/US2016/42531, dated Oct. 13, 2016, 11 pages.
Jones et al., "Replacing the complementarity-determining regions in a human antibody with those from a mouse," *Nature.*, 321:522-525, May 29, 1986.
Kashmiri et al., "SDR grafting—a new approach to antibody humanization," *Methods.*, 36:25-34, May 2005.
Knappik et al., "Fully synthetic human combinatorial antibody libraries (HuCAL) based on modular consensus frameworks and CDRs randomized with trinucleotides," *J Mol Biol.*, 296:57-86, Feb. 11, 2000.
Kohler & Milstein, "Continuous cultures of fused cells secreting antibody of predefined specificity," Nature., 256:495-497, Aug. 7, 1975.
Kovacevic et al., "Biological augmentation of rotator cuff tendon repair," Clin Orthop Relat Res., 466(3):622-633, Feb. 10, 2008.
Lazar et al., "A molecular immunology approach to antibody humanization and functional opti+A30:A36mization," Mol Immunol., 44(8):1986-1998, Mar. 2007.
Lonberg et al., "Antigen-specific human antibodies from mice comprising four distinct genetic modifications," *Nature.*, 368(6474):856-859, 1994.
Losman et al., "Baboon anti-idiotype antibodies mimic a carcinoembryonic antigen epitope," *Int J Cancer.*, 46:310-314, 1990.
Morikawa et al., "Contribution of oxidative stress to the degeneration of rotator cuff entheses," *J Shoulder Elbow Surg.*, 23(5):628-635, May 2014.
Nisonhoff et al., "Separation of univalent fragments from the bivalent rabbit antibody molecule by reduction of disulfide bonds," *Arch Biochem Biophys.*, 89(2):230-244, Aug. 1960.
Orlandi et al., "Cloning immunoglobulin variable domains for expression by the polymerase chain reaction," *Proc Natl Acad Sci USA.*, 86(10):3833-3837, May 1989.
Parenti et al., "Discovery of novel and selective SIRT6 inhibitors," *J Med Chem.*, 57(11):4796-4804, Jun. 12, 2014.
Porter, "The hydrolysis of rabbit y-globulin+A38:A41 and antibodies with crystalline papain," Biochem J., 73:119-126, 1959.
Radar et al., "A phage display approach for rapid antibody humanization Designed combinatorial V gene libraries," *Proc Natl Acad Sci USA*, 95:8910-8915, Jul. 1998.
Riechmann et al., "Reshaping human antibodies for therapy," *Nature.*, 332(6162):323-327, Mar. 24, 1988.
Rosok et al., "A combinatorial library strategy for the rapid humanization of anticarcinoma BR96 Fab," *J Biol Chem.*, 271(37):22611-22618, 1996.
Sandhu., "Protein Engineering of Antibodies," *Crit Rev Biotech.*, 12(5):437-462, 1992.
Shibuya et al., "Palladium and platinum nanoparticles attenuate aging-like skin atrophy via antioxidant activity in mice," *PLoS One.*, 9(10):e109288, 9 pages, Oct. 15, 2014.
Simons et al., "Patient information: Rotator cuff tendinitis and tear (Beyond the Basics)" (Jul. 18, 2013) [online] [retrieved on Sep. 15, 2016]. Retrieved from the Internet <URL: http:/Meb.archive.org/web/20130718152310/http://vvww.uptodate.com/contents/rotator-cufftendinitis-and-tear-beyond-the-basics?view=print> 26 pages.
Singer et al., "Optimal humanization of 1B4, an anti-CD18 murine monoclonal antibody, is achieved by correct choice of human V-region framework sequences," *J Immunol.*, 150(7):2844-2857, Apr. 1, 1993.
Summerton & Weller., "Morpholino Antisense Oligomers: Design, Preparation, and Properties," *Antisense Nucleic Acid Drug Development.*, 7:187-195, 1997.
Taylor et al., "Human immunoglobulin transgenes undergo rearrangement, somatic mutation and class switching in mice that lack endogenous IgM," *Int Immunol.*, 6(4):579-597, Apr. 1994.
Verhoeyen et al., "Reshaping human antibodies: Grafting an antilysozyme activity," *Science.*, 239:1534-1536, 1988.
Wellmark, "Prolotherapy" May 26, 2015,Retrieved online Sep. 15, 2016 from the Internet, URL: http://www.wellmark.com/Provider/MedpoliciesAndAuthorizations/MedicalPolicies/policies/Prolotherapy.aspx.
Winter et al., "Making antibodies by phage display technology," *Ann Rev Immunol.*, 12: 433-455, Apr. 1994.
U.S. Appl. No. 15/321,767, filed Dec. 23, 2016, 2017-0128534, May 11, 2017, Riester et al.
Cacchio et al., "Effectiveness of treatment of calcific tendinitis of the shoulder by disodium EDTA," Arthritis Care & Research, 61(1):84-91, Jan. 15, 2009.
Extended European Search Report in European Application No. 16825257.5, dated Feb. 1, 2019, 32 pages.
van der Sande et al., "Subacromial impingement syndrome: effectiveness of pharmaceutical interventions—nonsteroidal anti-inflammatory drugs, corticosteroid, or other injections: a systematic review,"Archives of physical medicine and rehabilitation, 94(5):961-976, Dec. 12, 2012.
Dean et al., "A systematic review of the histological and molecular changes in rotator cuff disease," Bone and Joint Research, 1(7):158-166, Jul. 2012.

* cited by examiner

TREATING ROTATOR CUFF CONDITIONS

CROSS-REFERENCE TO RELATED APPLICATIONS

This application is a National Stage application under 35 U.S.C. § 371 of International Application No. PCT/US2016/042531, having an International Filing Date of Jul. 15, 2016, which claims priority to U.S. Application Ser. No. 62/193,476, filed on Jul. 16, 2015. The disclosure of the prior applications are considered part of the disclosure of this application, and are incorporated in their entirety into this application.

BACKGROUND

1. Technical Field

This document provides methods and materials related to treating rotator cuff conditions (e.g., rotator cuff tendonitis or rotator cuff injuries such as partial or complete rotator cuff tears). For example, this document provides methods and materials for modulating zinc homeostasis using zinc or zinc chelators to treat rotator cuff conditions.

2. Background Information

The rotator cuff is a group of muscles and tendons that surround the shoulder joint, keeping the head of your upper arm bone firmly within the shallow socket of the shoulder. A rotator cuff injury can cause pain as well as loss of shoulder function.

SUMMARY

This document provides methods and materials related to treating rotator cuff conditions (e.g., rotator cuff tendonitis or rotator cuff injuries such as partial or complete rotator cuff tears). For example, this document provides methods and materials for modulating zinc homeostasis using zinc or zinc chelators to treat rotator cuff conditions. In some cases, a composition that includes zinc or one or more zinc chelators can be administered to (e.g., injected or infused into) the rotator cuff region of a mammal suffering from a rotator cuff condition. In some cases, a composition that includes zinc can be introduced at the time of a surgical repair. In such cases, the administered (e.g., injected) composition can reduce or reverse tendon degeneration, enhance healing, and/or increase tendon strength.

This document also provides methods and materials for using zinc or one or more zinc chelators to reduce the risk of developing a rotator cuff condition or to slow the progression of a rotator cuff condition. In some cases, a composition that includes zinc can be administered to (e.g., injected or infused into) the rotator cuff region of a mammal identified as being likely to develop a rotator cuff condition. In such cases, the administered (e.g., injected or infused) composition can prevent or slow the development of a rotator cuff condition.

In some cases, zinc or a zinc-chelator can be used alone or in conjunction with growth factors (e.g., FGFs or BMPs), epigenetic inhibitors (e.g., HDACs, SIRTs, and EZH2 inhibitors) other metals (e.g., Mg, Ca, or Se), or biomaterials (e.g., for controlled release of zinc) to treat a rotator cuff condition or to prevent or slow the development of a rotator cuff condition. For example, zinc or a zinc-chelator can be combined with one or more bioactive molecules as a solution or as part of a biocompatible scaffold or carrier to form a composition that is used to treat a mammal suffering from a rotator cuff condition.

In general, one aspect of this document features a method for treating a mammal having a rotator cuff condition. The method comprises, or consisting essentially of, administering a composition comprising, or consisting essentially of, zinc or a zinc chelator into a rotator cuff region of the mammal, wherein administration of the composition reduces or reverses tendon degeneration, enhances tendon healing, or increases tendon strength. The mammal can be a human. The rotator cuff condition can be a rotator cuff condition wherein a rotator cuff tendon is partially torn. The rotator cuff condition can be a rotator cuff condition wherein a rotator cuff tendon is ruptured. The rotator cuff condition can be rotator cuff tendonitis. The administering step can be an intra-articular injection into a joint space. The administering step can be an injection into a subacromial space. The administering step can be a direct injection into a damaged tendon. The composition can comprise zinc, wherein the zinc is ZnCl, zinc sulfate, zinc picolinate, zinc citrate, zinc glycerate, zinc gluconate, zinc acetate, or zinc monomethionine. The composition can comprise a zinc chelator. The composition can be housed within a device that controls the release of the composition within the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and from the claims.

DETAILED DESCRIPTION

This document provides methods and materials related to using zinc or one or more zinc chelators to treat rotator cuff conditions or to prevent or slow the development of rotator cuff conditions. For example, a composition that includes zinc can be administered to (e.g., injected or infused into) the rotator cuff region of a mammal suffering from a rotator cuff condition or identified as being likely to develop a rotator cuff condition. In such cases, the administered (e.g., injected or infused) composition can reduce or reverse tendon degeneration, enhance healing, increase tendon strength, and/or prevent or slow the development of a rotator cuff condition. Examples of different forms of zinc that can be used as described herein include, without limitation, ZnCl, zinc sulfate, zinc picolinate, zinc citrate, zinc glycerate, zinc gluconate, zinc acetate, and zinc monomethionine. Examples of zinc chelators that can be used as described herein include, without limitation, N,N,N',N'-tetrakis-(2-pyridylmethyl) ethylenediamine (TPEN), phenanthroline, EDTA, and EGTA.

Any appropriate rotator cuff condition can be treated as described herein. For example, rotator cuff tendonitis or rotator cuff injuries such as partial rotator cuff tears or rotator cuff ruptures can be treated as described herein. In addition, any appropriate mammal can be treated using the methods and materials described herein. For example, humans, monkeys, dogs, horses, sheep, pigs, goats, rabbits, rats or mice can be treated as described herein.

In some cases, a composition that includes zinc or one or more zinc chelators can be administered to a mammal by injecting or infusing the composition into the rotator cuff region of a mammal. For example, an injectable solution containing zinc or one or more zinc chelators can be injected into the rotator cuff region of a human suffering from a rotator cuff condition or identified as being likely to develop a rotator cuff condition. When injecting or infusing a composition that includes zinc or one or more zinc chelators into tissue of a mammal (e.g., a human), the composition can include a hydrogel, an aqueous solution, or ingredients that generate an isotonic solution (e.g., saline), or can be attached to an organic scaffold. The composition can have a pH that is at or near a physiological neutral pH (e.g., pH 6-8). In some cases, zinc, for example, in the form of ZnCl or $ZnSO_4$, a chelated form of zinc, and/or a zinc chelator can be formulated into a composition for injection or infusion into the rotator cuff region of a mammal.

A composition provided herein (e.g., a composition containing zinc or a zinc chelator) can be administered to a rotator cuff region of a mammal by intra-articular injection into the joint space, injection into the subacromial space, direct injection into damaged tendons, delivery as a topical at the time of surgical repair that could include delivery to the tendon itself, delivery to the bone tendon interface, or delivery directly into the joint space. In some cases, a composition provided herein (e.g., a composition containing zinc or a zinc chelator) can be administered to a rotator cuff region of a mammal using a suture coated with or containing zinc or a zinc chelator placed into the joint, adjacent to the tendon, or at the bone tendon interface.

In some cases, a composition that includes zinc or a zinc chelator can be administered to a mammal orally, topically, or systemically (e.g., intravenously, via general injection, or intranasally via a nasal spray). For example, a pill or capsule containing zinc can be orally administered to a human suffering from a rotator cuff condition or identified as being likely to develop a rotator cuff condition. When administering a composition that includes zinc orally to a mammal (e.g., a human), the composition can include zinc sulfate, zinc picolinate, zinc citrate, zinc glycerate, zinc gluconate, zinc acetate, or zinc monomethionine.

In some cases, a composition that includes zinc or a zinc chelator can include zinc or the zinc chelator as the sole active ingredient or can include other active ingredients for treating rotator cuff conditions. For example, a composition that includes zinc or a zinc chelator can include growth factors (e.g., FGFs or BMPs), epigenetic inhibitors (e.g., HDACs, SIRTs, or EZH2 inhibitors), minerals (e.g., Mg, Ca, or Se), biomaterials (e.g., biomaterials for controlled release of zinc), stem cells (e.g., bone marrow derived or adipose-tissue derived stem cells), or combinations thereof as active ingredients for treating a rotator cuff condition.

An effective amount of a composition containing zinc can be any amount that reduces the severity of a symptom of a condition being treated (e.g., a rotator cuff condition), reduces the risk of developing a rotator cuff condition, or slows the progression of a rotator cuff condition without producing significant toxicity to the mammal. For example, an effective amount of zinc can be from about 0.1 pM to about 100 mM (e.g., from about 100 pM to about 100 mM, from about 10 nM to about 100 mM, from about 1 mM to about 100 mM, from about 1 nM to about 10 mM, or from about 10 nM to about 1 mM). In some cases, between about 1 fg and about 2 mg of zinc can be administered to an average sized human (e.g., about 60-85 kg human) daily for about four to about eight weeks (e.g., about five to six weeks). If a particular mammal fails to respond to a particular amount, then the amount of zinc can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., rotator cuff condition) may require an increase or decrease in the actual effective amount administered.

The frequency of administration can be any frequency that reduces the severity of a symptom of a condition to be treated (e.g., a rotator cuff condition), reduces the risk of developing a rotator cuff condition, or slows the progression of a rotator cuff condition without producing significant toxicity to the mammal. For example, the frequency of administration can be from about three times a day to about once a month. In some cases, a one-time administration (e.g., before, during, or after surgery) can be administered. The frequency of administration can remain constant or can be variable during the duration of treatment. In some cases, zinc can be administered using a continual slow release from a device (e.g., a scaffold) placed into the mammal (e.g., a human) during surgery. A course of treatment with a composition containing zinc can include rest periods. For example, a composition containing zinc can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., a rotator cuff condition) may require an increase or decrease in administration frequency.

An effective duration for administering a composition containing zinc can be any duration that reduces the severity of a symptom of the condition to be treated (e.g., a rotator cuff condition), reduces the risk of developing a rotator cuff condition, or slows the progression of a rotator cuff condition without producing significant toxicity to the mammal. Thus, the effective duration can vary from several days to several weeks, months, or years. In general, the effective duration for the treatment of a rotator cuff condition can range in duration from several weeks to the mammal's lifetime. Multiple factors can influence the actual effective duration used for a particular treatment. For example, an effective duration can vary with the frequency of administration, effective amount, use of multiple treatment agents, route of administration, and severity of the condition being treated.

In some cases, the methods and materials provided herein (e.g., a composition containing zinc) can be used to treat tendonitis or a tendon disorder such as an Achilles tendon disorder, a patellar tendon disorder, a quadriceps tendon disorder, or an epicondylitis.

The invention will be further described in the following examples, which do not limit the scope of the invention described in the claims.

EXAMPLES

Example 1—Assessment of Damaged/Ruptured Rotator Cuff Tendons

High throughput RNA-sequencing of intact and ruptured rotator cuff tendons was performed. The sequencing analysis revealed that degenerating rotator cuff tissue exhibit changes in the expression levels of many zinc-related polypeptides (Table 1).

TABLE 1

Expression of zinc-related genes in rotator cuff tendon.

| Gene | Fold Change Intact vs Diseased Tendon |
|---|---|
| ZNF131 | 7.74495203 |
| ZNF224 | 7.7104387 |
| ZNF354C | 7.33998444 |
| ZNF718 | 7.23646262 |
| MT1B | 0.121312 |
| CRIP2 | 0.180982 |
| CRIP1 | 0.086645 |
| MT3 | 0.00438 |
| MT1H | 0.096981 |

These results demonstrate that zinc deficiency and concomitant oxidative responses are involved in rotator cuff degeneration. These results also demonstrate that zinc supplementation (via oral administration or injection or infusion into rotator cuff tissue) can mitigate or reverse rotator cuff degeneration and associated pathological conditions (e.g., rotator cuff tears and tendonopathy).

Example 2—Injecting Zinc to Treat Damaged/Ruptured Rotator Cuff Tendons

About 1-2 mg of zinc is formulated with 1 to 10 mL of saline or other soluble solution to obtain a liquid composition. About 0.25 mL to about 1 mL of this liquid composition is injected directly into degenerative or surgically repaired tendons or into the joint space to deliver zinc to the target tissue.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having a rotator cuff condition, wherein said method comprising administering a composition comprising N,N,N',N'-tetrakis-(2-pyridylmethyl) ethylenediamine into a rotator cuff region of said mammal, wherein administration of said composition reduces or reverses tendon degeneration, enhances tendon healing, or increases tendon strength.

2. The method of claim 1, wherein said mammal is a human.

3. The method of claim 1, wherein said rotator cuff condition is a rotator cuff condition wherein a rotator cuff tendon is partially torn.

4. The method of claim 1, wherein said rotator cuff condition is a rotator cuff condition wherein a rotator cuff tendon is ruptured.

5. The method of claim 1, wherein said rotator cuff condition is rotator cuff tendonitis.

6. The method of claim 1, wherein said administering step is an intra-articular injection into a joint space.

7. The method of claim 1, wherein said administering step is an injection into a subacromial space.

8. The method of claim 1, wherein said administering step is a direct injection into a damaged tendon.

9. The method of claim 1, wherein said composition further comprises zinc, and wherein said zinc is ZnCl, zinc sulfate, zinc picolinate, zinc citrate, zinc glycerate, zinc gluconate, zinc acetate, or zinc monomethionine.

10. The method of claim 1, wherein said composition is housed within a device that controls the release of said composition within said mammal.

* * * * *